(12) United States Patent
Shinoda et al.

(10) Patent No.: US 8,877,483 B2
(45) Date of Patent: Nov. 4, 2014

(54) DIOXIN ELIMINATION PROMOTER

(75) Inventors: Tadashi Shinoda, Kanagawa (JP);
Akihiro Masuyama, Kanagawa (JP);
Hidetoshi Morita, Kanagawa (JP);
Hiroshi Yoshikawa, Tokyo (JP)

(73) Assignee: Calpis Co., Ltd., Tokyo (JP)

( * ) Notice: Subject to any disclaimer, the term of this patent is extended or adjusted under 35 U.S.C. 154(b) by 811 days.

(21) Appl. No.: 10/514,555

(22) PCT Filed: May 30, 2003

(86) PCT No.: PCT/JP03/06883
§ 371 (c)(1),
(2), (4) Date: May 27, 2005

(87) PCT Pub. No.: WO03/101472
PCT Pub. Date: Dec. 11, 2003

(65) Prior Publication Data
US 2005/0201997 A1    Sep. 15, 2005

(30) Foreign Application Priority Data

May 31, 2002  (JP) .................................. 2002-160055

(51) Int. Cl.
| C12N 1/20 | (2006.01) |
| A61K 49/00 | (2006.01) |
| A61K 39/07 | (2006.01) |
| C12R 1/225 | (2006.01) |
| A61K 35/74 | (2006.01) |
| A23L 1/30 | (2006.01) |
| C12R 1/125 | (2006.01) |
| A23K 1/00 | (2006.01) |

(52) U.S. Cl.
CPC .............. *C12R 1/225* (2013.01); *A61K 35/742* (2013.01); *A23L 1/3014* (2013.01); *C12R 1/125* (2013.01); *A23K 1/009* (2013.01); *A61K 35/744* (2013.01)
USPC ................. 435/252.31; 424/234.1; 424/246.1; 424/9.1; 424/9.2

(58) Field of Classification Search
USPC .............. 424/78.01, 93.1, 93.4, 93.46, 234.1, 424/278.1; 426/2, 61, 63, 531, 665; 435/139, 173.1, 221, 222, 252.31, 435/252.4, 252.5, 485
See application file for complete search history.

(56) References Cited

FOREIGN PATENT DOCUMENTS

| CA | 2 408 968 A1 | 11/2002 | |
| EP | 0287699 | * 4/1987 | ............... C12N 1/20 |
| EP | 0 287 699 | 10/1988 | |
| EP | 1304114 | 4/2003 | |
| JP | 9-234021 | 9/1997 | |
| JP | 11-347533 | 12/1999 | |
| JP | 11-347553 | 12/1999 | |
| JP | 2000-232878 | 8/2000 | |
| JP | 2001-61452 | 3/2001 | |
| KR | 1996-0001472 | 1/1996 | |
| KR | 2002-0007575 | 1/2002 | |
| WO | 98/54981 | 12/1998 | |
| WO | WO 98/54981 | * 12/1998 | ............... A23K 1/16 |
| WO | 99/26736 | 6/1999 | |
| WO | 99/57243 | 11/1999 | |
| WO | 01/05927 | 1/2001 | |
| WO | 01/87317 | 11/2001 | |

OTHER PUBLICATIONS

McMichael J Epidemiol Community Health 1999; 53; 742-743.*
Arnold Schecter et. al., Journal of Toxicology and Environmental Health, Part A, 63:1-18.*
Habeck. Toxicological Profile for Dioxin Jun. 1989. Agency for Toxic Substances and Disease Registry; United States Public Health Service. Eco-USA Copyright 1996-2010(www.eco-usa.net/toxics/chemicals/dioxin.shtml).*
Morita, Kunimasa et al. "Effect of Chlorella, Spirulina and Chlorophyllin on Fecal Excretion of Polychlorinated Dibenzo-p-dioxins in Rats", Journal of Health Science, vol. 43, No. 1, pp. 42-47, with English abstract 1997.
"High Fibrous Diet Helpful for Elimination of Dioxin", China Health Products, No. 6, 1999, p. 43 (with English Abstract).
Office Action issued on Sep. 14, 2010, in Japanese Patent Application No. 2004-508827 (with English translation).
Chinese Office Action issued Jan. 19, 2011, in Patent Application No. 200810215935.6 (with English-language translation).
Office Action issued Jul. 13, 2012 in Norwegian Patent Application No. 20045238 (with English-language translation).
Office Action issued Jul. 24, 2012 in European Patent Application No. 03 733 214.5.
Kaoru Yamazaki, et al., "Effect of oral administration of 3,3',4,4',5-pentachlorobiphyenl on the intestinal microbiota of Sprague-Dawley rats", Animal Science Journal, Japanese Society of Animal Science, vol. 79, No. 3, XP-002535929, 2008, pp. 391-400.
Morita, Kunimasa et al. "Effect of Chiorella, Spinulina and Chlorophyllin on Fecal Excretion of Polychlorinated Dibenzo-p-dioxins in Rats", Journal of Health Science, vol. 43, No. 1, pp. 42-47, with English abstract.
Office Action issued on Jan. 5, 2012 in the corresponding Norwegian Patent Application No. 20045238 (with English-language Translation).

(Continued)

*Primary Examiner* — Rodney P Swartz

(74) *Attorney, Agent, or Firm* — Oblon, Spivak, McClelland, Maier & Neustadt, L.L.P.

(57) ABSTRACT

An accelerating agent for elimination of dioxins which comprises, as an active ingredient, a microorganism having an activity of accelerating elimination of dioxins in the body to the outside of the body.

23 Claims, 4 Drawing Sheets

(56) References Cited

OTHER PUBLICATIONS

Office Action issued on Aug. 12, 2011 in European Patent Application No. 03 733214.5-1212.

Tolerable Daily Intake (TDI) of dioxins (26 pages, Japanese Publication), Jun. 1999.
Biosci. Biotechnol. Biochem., 70(12), 2974-2981, 2006 (8 pages).

* cited by examiner

STRAIN A: *Lactobacillus* sp CP3012(FERM BP-8052)
STRAIN B: *Bacillus subtilis* C-3102(FERM BP-1096)

DIOXIN ELIMINATION PROMOTER

TECHNICAL FIELD

The present invention relates to an accelerating agent for elimination of dioxins comprising, as an active ingredient, a microorganism having an activity of eliminating dioxins that are unintentionally absorbed into and accumulated in the body to the outside of the body.

BACKGROUND ART

Endocrine disrupting chemicals, so-called environmental hormones, have become a focus of worldwide social interest since their existence was shown in *Our Stolen Future* (Japanese title: *Ubawareshimirai,* 1st Edition issued in 1996, revised in 2001) by Theo Colborn et al. A great number of chemical substances suspected to have an endocrine disrupting activity have been known, chemical substances including polychlorodibenzo-p-dioxins (PCDDs), polychlorinated dibenzofurans (PCDFs) and co-planar polychlorinated biphenyls (cPCBs) were defined in Japan as the dioxins by *Law Concerning Special Measures against Dioxins* published in July, 1999. The dioxins have a very high toxicity. Known acute toxicity includes dermatitis, hepatopathy, neuropathy, immunologic toxicity and the like, and suspected chronic toxicity includes teratogenicity, embryotoxicity, carcinogenicity, xenobiotic metabolic enzyme induction and the like. It is estimated that the amount of the dioxins to which a human is exposed in the daily life is at a level of about 2.3 pg-TEQ (toxic equivalent quantity), which is far lower than the amount showing acute toxicity. However, since it is known that the dioxins are remained and accumulated in the adipose tissue in the living body, there is a possibility that they act like internally synthesized hormones at a concentration lower than the toxically active concentration. This activity is the reason why the dioxins are called environmental hormones.

Most of the dioxins are released to the environment through an unintentional production process. cPCBs were contained as by-products in polychlorobiphenyls (PCBs) used in a great amount in electric parts and the like owing its incombustibility and insulative property, and resultingly, was continuously released to the environment even after its production was prohibited in 1971. While the dioxins are very slowly decomposed in the environment, they are taken into living bodies of various organisms during the decomposition period and bioconcentrated within the food chain. It is afraid that humans are unavoidably exposed to them by taking polluted organisms as food.

There are many unclear points relating to absorption, metabolism and exclusion of the dioxins in living bodies. Since the dioxins are oil-soluble, they are transferred to the adipose tissue after taken in the body as described above. Particularly, in liver, expression of a specific gene is induced by a signal transduction pathway through a receptor. Especially, it has been shown that, when cytochrome P450 protein is expressed, the dioxins are hydroxylated or reductively dehalogenated by its enzymatic activity. Thus, it is considered that the dioxins are excluded to the outside of the body owing to enhancement of water-solubility by such metabolism and through secretion into the bile.

On the other hand, microorganisms such as lactic acid bacteria used for fermented milk and *Bacillus subtilis* used for fermented soybeans (natto) have been widely utilized in foods and feeds, and it is known that many advantageous activities were brought about to a host by their cells and fermentation products. Particularly, lactic acid bacteria, *Bacillus subtilis* and bifidobacteria contribute to health of the host by directly or indirectly acting on intestinal flora and eliminating harmful bacteria. In addition, as an activity without relating to intestinal flora, it is known that a peptide as a fermentation product has an antihypertensive activity. Inventions in which lactic acid bacteria give advantageous activities to liver function include a lactic acid bacterium which lowers liver cholesterol (JP-A-7-250670), a fermentation product of an enzymatically treated rice bran lactic acid bacterium which relieves hepatopathy caused by stress (JP-A-9-132533), an intestinal infusion solution containing *Lactobacillus plantarum* and arginine in combination (JP-A-11-504936) and the like. However, no microorganisms relating to elimination of environmental pollution substances to the outside of the living body have been known.

An object of the present invention is to provide an accelerating agent for elimination of dioxins, which comprises, as an active ingredient, a microorganism having an activity of accelerating elimination of dioxins accumulated in the body such as liver to the outside of the body. Since the dioxins are unconsciously taken from foods, the air, water, soil or the like, and its intake is difficult to avoid, and it is important that the active ingredient is used in daily eating in humans and is a feed additive routinely usable in edible livestock.

DISCLOSURE OF THE INVENTION

The present invention relates to the following (1) to (12):

(1) An accelerating agent for elimination of dioxins, which comprises, as an active ingredient, a microorganism having an activity of accelerating elimination of dioxins in the body to the outside of the body.

(2) The accelerating agent according to (1), wherein the microorganism is a lactic acid bacterium.

(3) The accelerating agent according to (1), wherein the microorganism is nonpathogenic *Bacillus*.

(4) A method for accelerating elimination of dioxins, which comprises administering to a human or an animal a microorganism having an activity of accelerating elimination of dioxins in the body to the outside of the body.

(5) The method according to (4), wherein the microorganism is a lactic acid bacterium.

(6) The method according to (4), wherein the microorganism is nonpathogenic *Bacillus*.

(7) Use of a microorganism having an activity of accelerating elimination of dioxins in the body to the outside of the body for accelerating elimination of dioxins.

(8) Use of a microorganism having an activity of accelerating elimination of dioxins in the body to the outside of the body for the manufacture of an accelerating agent for elimination of dioxins.

(9) The use according to (7) or (8), wherein the microorganism is a lactic acid bacterium.

(10) The use according to (7) or (8), wherein the microorganism is nonpathogenic *Bacillus*.

(11) The accelerating agent according to any one of (1) to (3), wherein an effective cell number of the microorganisms is $5 \times 10^6$ cells/kg body weight or more.

(12) The accelerating agent according to (1), wherein the microorganism is *Lactobacillus* sp CP3012 (FERM BP-8052).

(13) The accelerating agent according to (1), wherein the microorganism is *Bacillus subtilis* c-3102 (FERM BP-1096).

(14) The accelerating agent according to any one of (1) to (3) or (11) to (13), wherein the dioxins are the dioxins defined in "regulation of special measures for dioxins" promulgated in Japan in July in 1999.

(15) The method according to any one of (4) to (6), wherein an effective cell number of the microorganism is $5\times10^6$ cells/kg body weight or more.

(16) The method according to (4), wherein the microorganism is *Lactobacillus* sp CP3012 (FERM BP-8052).

(17) The method according to (4), wherein the microorganism is *Bacillus subtilis* c-3102 (FERM BP-1096).

(18) The method according to any one of (4) to (6), wherein the dioxins are the dioxins defined in "regulation of special measures for dioxins" promulgated in Japan in July in 1999.

(19) The use according to any one of (7) to (10), wherein an effective cell number of the microorganism is $5\times10^6$ cells/kg body weight or more.

(20) The use according to (7) or (8), wherein the microorganism is *Lactobacillus* sp CP3012 (FERM BP-8052).

(21) The use according to (7) or (8), wherein the microorganism is *Bacillus subtilis* c-3102 (FERM BP-1096).

(22) The use according to any one of (7) to (10), wherein the dioxins are the dioxins defined in "regulation of special measures for dioxins" promulgated in Japan in July in 1999.

(23) A physiologically functional foodstuff, which comprises the accelerating agent according to any one of (1) to (3) or (11) to (14).

(24) The use of the accelerating agent according to any one of (1) to (3) or (11) to (14) for the manufacture of a physiologically functional foodstuff.

BEST MODE FOR CARRYING OUT THE INVENTION

Figure 1:
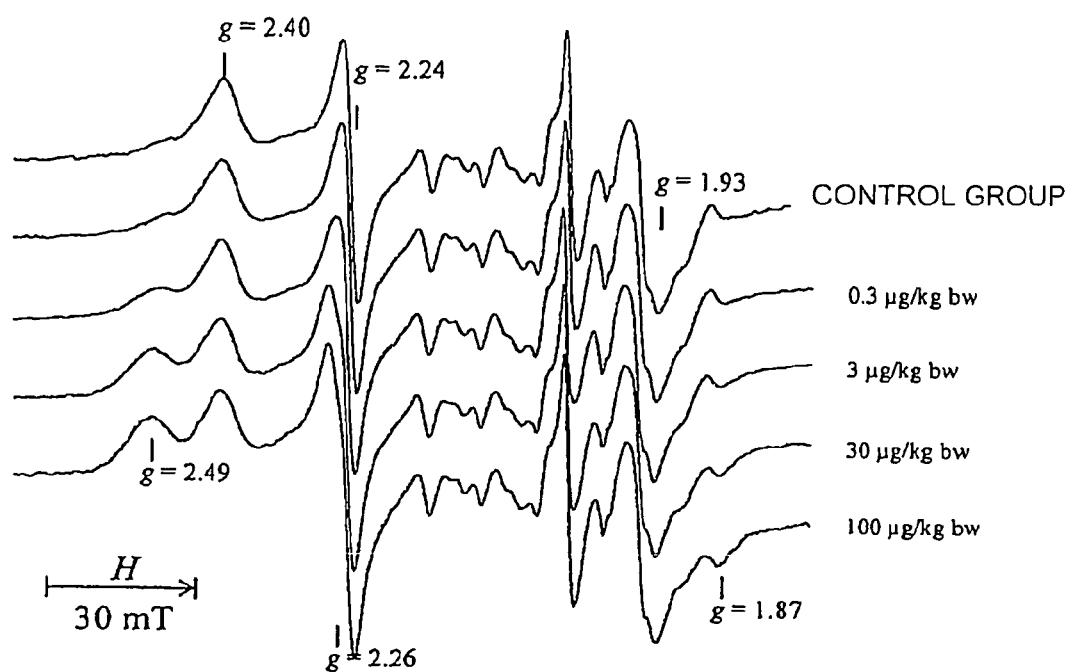
FIG. 1 shows EPR spectra of rat liver after oral administration of PCB126.

The inventors of the present invention have found that denaturation, caused by dioxins, of liver cytochrome P450, which is supposed to contribute to metabolic exclusion of the dioxins, can be relieved by oral administration of a microorganism, so that elimination of the dioxins from the inside of the body can be accelerated, and thus have completed the present invention.

The microorganism having an activity of accelerating elimination of dioxins accumulated in the body to the outside of the body according to the present invention (hereinafter referred to as the "microorganism of the present invention") is (1) a microorganism which can be administered to a rat to which dioxins have been administered, and (2) a microorganism selected by detecting suppression of an abnormal P450 molecule in the measurement by electron paramagnetic resonance (EPR) of the liver tissue after administration of the microorganism for a predetermined period.

Since the accelerating agent for elimination of dioxins according to the present invention (hereinafter referred to as the "accelerating agent of the present invention") accelerates elimination of the dioxins accumulated in the body, it is advantageous that the effect is expected even in the intake after exposure in comparison with preventive agents such as an absorption inhibitor for dioxins.

The dioxins are not particularly limited, and include those which are generally classified into dioxins. Specific examples include polychlorodibenzo-p-dioxins (PCDDs), polychlorinated dibennzofurans (PCDFs), co-planar polychlorinated biphenyls (cPCBs), isomers thereof, and the like.

Associate professor Dr. Morita, Faculty of Veterinary Medicine, Azabu University, found that in cytochrome P450 protein of dioxin-taken rats, there is a possibility that the enzymatic activity is inhibited by coordination of histidine in the protein molecule itself to sixth locus of coordination which participates enzymatic activity (Hidetoshi Morita et al., 98th Convention of Japanese Society of Animal Science, X30-21, 2001). This change can be monitored by an EPR measurement method.

The EPR measurement method is also called electron spin resonance (ESR) measurement method. Status of electrons in substance and status of environment containing the electrons can be examined by utilizing movement of magnetic moment carried by the electrons. Since a measurable substance must have an unpaired electron, the selectivity for the measurement is high. In addition, since the measurement is carried out in a constant magnetic field of 1 T or less and a microwave oscillating magnetic field of 0.1 mT or less, the specimen is exposed to a low energy and a nondestructive measurement can be carried out. The principle of the ESR measurement method is as follows: When an atom or a molecule having an unpaired electron is placed in a magnetic field, the electron enters in a low energy orbital. When a microwave oscillating magnetic field having a higher frequency is applied, the unpaired electron transits to the higher energy orbital. The transition between orbitals is observed as absorption of microwave. At this time, g-value is a factor showing a magnetic field where a resonance is observed. The g-value is indicated as a position on a measuring chart and is an important element for investigating the electron state of the molecule to be measured.

When the EPR measurement is carried out with rat liver as an experimental animal, the resonance absorption of an iron atom contained in cytochrome P450 protein is observed at a position of g=2.40. When dioxin were administered to a rat, an abnormal resonance absorption which is not observed in untreated case appears as a signal at a position of g=2.49, in addition to the normal resonance absorptions. Since the intensity of the abnormal signal becomes higher according to increase of an amount of dioxins administered, it can be a living body index showing a degree of pollution.

The microorganism of the present invention may be any microorganism, so long as it is a microorganism that can normalize the abnormal signal at the position of g=2.49 derived from dioxins in the EPR measurement. Specific examples include bacteria, yeasts and the like.

The accelerating agent of the present invention preferably contains microorganisms so as to give an effective cell number at $5\times10^9$ cells/kg body weight or more when it is administered to a human or an animal.

The microorganism of the present invention can be utilized as various fermentation foods depending on properties of the microorganism.

When the microorganism is a lactic acid bacterium, it can be used in the form of a dairy product such as fermented milk, yogurt, lactic acid drink and acidophilus milk and the like, and each of which can be converted to an easily utilizable form by suitably adding sugar, a sour agent, a flavor and the like. In addition, so long as the effective cell number is contained, the effective microorganism can be freeze-dried to form a powdered microorganism preparation or be tableted to form a tablet preparation so that it can be orally administered easily.

So long as the microorganism is contained at an effective cell number, solid fermentation products such as fermented soybeans (natto) and rice malt can be used in addition to liquid fermented milk. Therefore, the product is expected to routinely taken without difficulty.

In addition, the product can contain a carrier acceptable in the preparation of medicaments, foods, feeds or the like. For example, liquid preparations such as syrup can be produced using water; saccharides such as sucrose, sorbitol and fructose; glycols such as polyethylene glycol and propylene glycol; oils such as sesame oil, olive oil and soybean oil; preservatives such as p-hydroxybenzoic acid esters; flavors such as strawberry flavor and peppermint; and the like. Furthermore, tablets, powders and granules can be produced using excipients such as lactose, glucose, sucrose and mannitol; disintegrants such as starch and sodium alginate; lubricants such as magnesium stearate and talc; binders such as polyvinyl alcohol, hydroxypropylcellulose and gelatin; surfactants such as fatty acid esters; plasticizers such as glycerol; and the like.

Additionally, a disrupted cell or a cell extract of the microorganism of the present invention can be used as the active ingredient in the accelerating agent of the present invention, so long as it has an activity of accelerating elimination of dioxins according to the present invention.

The microorganism of the present invention may either be a viable cell or a dead cell, and a viable cell is preferable.

The accelerating agent of the present invention can be administered to a human or a non-human animal (feedstock such as cow, pig and chicken, farmed fishes, etc.) alone or as an additive to other foods, drinks, feeds or the like.

A dose is changed depending on the kind of animals to be subjected, their symptoms and the like. In general, it is administered once or several times generally at $10^6$ cells/kg body weight or more, preferably $5 \times 10^9$ cells/kg body weight or more, per day. The upper limit of the dose is not particularly limited.

Examples of microorganism selected in such a manner include lactic acid bacterium described below. This lactic acid bacterium is a mere example and the scope is not limited to the strain of the lactic acid bacterium.

Lactic acid bacterium: *Lactobacillus* sp CP3012 (FERM BP-8052)
Morphological Property:
1) Morphology: short rod
2) Motility: no
3) Spore: no
4) Gram staining: positive.
Culture Property:
Culture conditions: Litmus milk, 30° C.
1) Coagulation: no
2) Liquefaction: no
3) Acid production: yes
4) Viable pH range: pH 5-7
5) Viable temperature: 15-45° C.
Physiological Property
1) Catalase: negative
2) Indole production: negative
3) Nitrate reduction: negative
4) Attitude to oxygen: facultative anaerobic
5) Growth at 15° C.: yes
6) Denitrification: negative
7) MR test: positive
8) VP test: negative
9) Hydrogen sulfide production: negative
10) Starch hydrolysis: negative
11) Citrate assimilation (Koser): positive, (Christensen): negative
12) Nitrate assimilation: negative
13) Ammonium salt assimilation: negative
14) Pigment production: negative
15) Urease activity: negative
16) Oxidase activity: negative
17) O-F test: positive in both aerobic and anaerobic
18) Results of acid production test from various saccharides (aerobic culture with ammonium-saccharide medium (ASS; Smith, N. R., Gordon, R. E. and Clark, F. E. (1952), Aerobic sporeforming bacteria; Monograph, No. 16, Washington, D.C.: U.S. Dep. Agriculture) as a basal medium) are as follows:

| glucose | + | xylose | − |
|---|---|---|---|
| lactose | + | trehalose | + |
| mannose | + | inositol | − |
| fructose | + | mannitol | + |
| galactose | + | sorbitol | − |
| sucrose | + | starch | − |
| arabinose | + | glycerol | − |
| maltose | + | | |

19) Gas production from various saccharides are as follows:

| glucose | − | xylose | − |
|---|---|---|---|
| lactose | − | trehalose | − |
| mannose | − | inositol | − |
| fructose | − | mannitol | − |
| galactose | − | sorbitol | − |
| sucrose | − | starch | − |
| arabinose | − | glycerol | − |
| maltose | − | | |

The lactic acid bacterium, *Lactobacillus* sp CP3012, has been deposited as FERM BP-8052 on May 27, 2002 in International Patent Organism Depositary, National Institute of Advanced Industrial Science and Technology (AIST Tsukuba Central 6, 1-1, Higashi 1-chome, Tsukuba-shi, Ibaraki-ken, 305-8566 Japan).

Examples of microorganism selected in such a manner include nonpathogenic *Bacillus* such as *Bacillus subtilis* c-3102. *Bacillus subtilis* c-3102 has been deposited as FERM BP-1096 on Jun. 28, 1986 in Fermentation Research Institute, Agency of Industrial Science and Technology (1-3, Higashi 1-chome, Yatabe-machi, Tsukuba-gun, Ibaraki-ken, 305 Japan) (now International Patent Organism Depositary, National Institute of Advanced Industrial Science and Technology (AIST Tsukuba Central 6, 1-1, Higashi 1-chome, Tsukuba-shi, Ibaraki-ken, 305-8566 Japan)). This nonpathogenic *Bacillus* is a mere example and the scope is not limited to the strain of the nonpathogenic *Bacillus*.

Example

Construction of Model Animals

As laboratory animals, rats to which PCB 126 (3,3',4,4',5-pentachlorobiphenyl) had been administered were prepared. The rats were 6-week-old Sprangue-Dawley (purchased from Nippon Charles River). After acclimation rearing for about one week, they forcedly administered with solutions containing an adequate concentration of PCB 126 (manufactured by Wellington Laboratories; purity: 99.99% or more) dissolved in commercially available corn oil (manufactured by Hayashi Chemicals) so that the amount of cPCB was 0 (control), 0.3, 3, 30 or 100 μg/kg body weight (bw) in the same amount of corn oil through a probe. PCB-administered rats were euthanized with ether 24 hour after the administration. The liver was isolated and sufficiently perfused with 1.15% KCl buffer. Then, tissue fragments were analyzed by an EPR measurement method.

EPR Measurement:

Apparatus for EPR measurement was JES-TE300 (manufactured by JEOL) and measurement was carried out according to the manufacture's instruction under the following conditions:

| | |
|---|---|
| Temperature: | 77 K. |
| Frequency: | 9.11 GHz |
| Power: | 10 mW |
| Sweep Time: | 4 min. |
| Modulation Width: | 0.32 mT |
| Time Constant: | 0.3 sec. |
| Field: width | 300 ± 100 mT |

FIG. 1 shows EPR spectrum patterns of rat liver tissue fragments to which cPCB had been administered. In the spectra, a signal at g=2.40 is a peak derived from a heme iron atom in normal cytochrome P450. A preceding specific peak appears as shown by a signal at g=2.49. It can be understood that its intensity varies depending on the administered amount.

Figure 2:
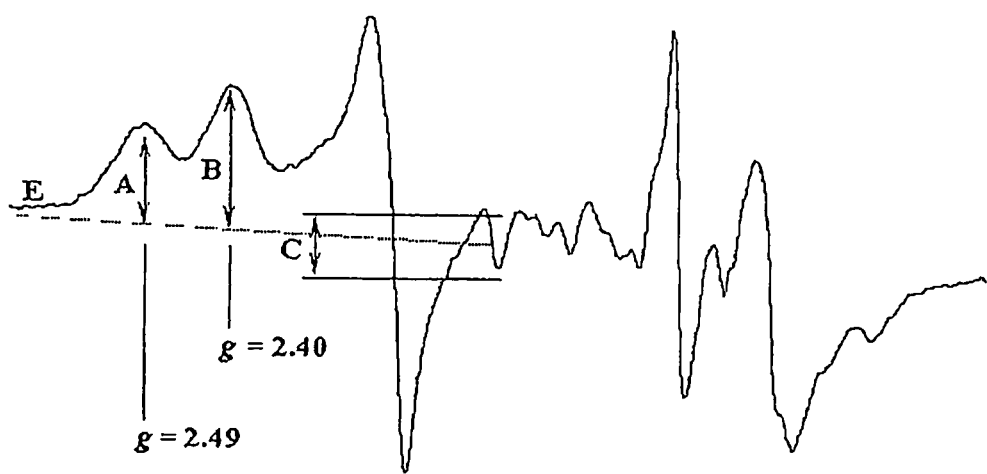
FIG. 2 shows a typical EPR signal chart after administration of cPCB.

Numeration:

In order to represent data for intensity of signals at g=2.40 and g=2.49 as numbers, standardization was applied. Intensity of signals derived from a manganese atom shown by C in FIG. 2, which was a schematic diagram showing a typical signal chart, was taken as the standard. It is known that an amount of manganese atoms contained in liver is hardly affected by an amount of manganese atoms in diet [Sakurai et al., *Biochem. Biophys. Acta*, 841, 208-214 (1985)]. Therefore, the difference between the maximum value and the minimum value in peak C was taken as $H_c$ and the central point $H_{cen}$ of $H_c$ was determined. Points connecting $H_{cen}$ and "the mean value of the 30 sampling points" at a lower side than the signal A in magnetic field, shown by E in the graph, were joined together with a line segment, and the lengths of perpendicular lines from the peaks at g=2.49 and g=2.40 on said line segment were taken as $H_A$ and $H_B$, respectively. In order to take the weights of samples used in the measurement into consideration, $H_A$ and $H_B$ were divided by $H_C$, and thus the intensity of the signal at g=2.49 was expressed as $H_A/H_C$ and the intensity of the signal at g=2.40 was expressed as $H_B/H_C$.

Microorganism Strains:

Strains *Lactobacillus* sp CP3012 (FERM BP-8052) and *Bacillus subtilis* c-3102 (FERM BP-1096) were used as a lactic acid bacterium and *Bacillus subtilis*, respectively. *Bacillus subtilis* c-3102 has been deposited as FERM BP-1096 on Jun. 28, 1986 in Fermentation Research Institute, Agency of Industrial Science and Technology (1-3, Higashi 1-chome, Yatabe-machi, Tsukuba-gun, Ibaraki-ken, 305 Japan) (now International Patent Organism Depositary, National Institute of Advanced Industrial Science and Technology (AIST Tsukuba Central 6, 1-1, Higashi 1-chome, Tsukuba-shi, Ibaraki-ken, 305-8566 Japan)).

Culture of Microorganism:

For pure culture of the microorganisms, a common process can be used with a medium adequate for the respective microorganism used. When the microorganism is a lactic acid bacterium of *Lactobacillus*, a medium prepared with MRS medium (manufactured by Difco) according to the manufacture's instruction was used. When it was *Bacillus subtilis*, a trypticase soy medium (manufactured by BBL) was used. The lactic acid bacterium of *Lactobacillus* was stationally cultured at 37° C. under anaerobic conditions, and *Bacillus subtilis* was cultured by shaking culture at 37° C.

In all the culture, cell numbers were measured with a hemacytometer (Thoma counting chamber, manufactured by Kayagaki Irikakogyo Ltd.) according to the manufacture's instructions.

Preparation of Specimen to be Administered:

1. Fermented Milk-like Specimen

Milk, skim milk, reconstituted skim milk or the like is sterilized at a temperature arriving to 98° C. After cooling to 37° C., lactic acid of food additive grade (122-01936 of Wako Pure Chemical Ind., Ltd., etc.) was gradually added under stirring by propellers or the like to adjust pH to 4.5. Similar homogenization with the homogenizer as described above gave a fermented milk-like specimen.

2. Cell-added Fermented Milk-like Specimen

Each of the above described microorganisms cultured separately was suspended in the above fermented milk-like specimen to give a cell concentration of $1 \times 10^9$ cells/ml to give a cell-added fermented milk-like specimen.

Administration Test:

The specimen containing a microorganism was administered to the PCB 126-administered rat described above for 60 days. The dose was 5 ml/kg body weight and at least the administration was continued during week days (5 days, from Monday to Friday). After the administration period was over, the rat was euthanized and the liver was isolated. After sufficient perfusion with 1.15% KCl buffer solution, the tissue was applied to analysis by the EPR measurement method and measurement of a CPCB concentration.

Figure 3:
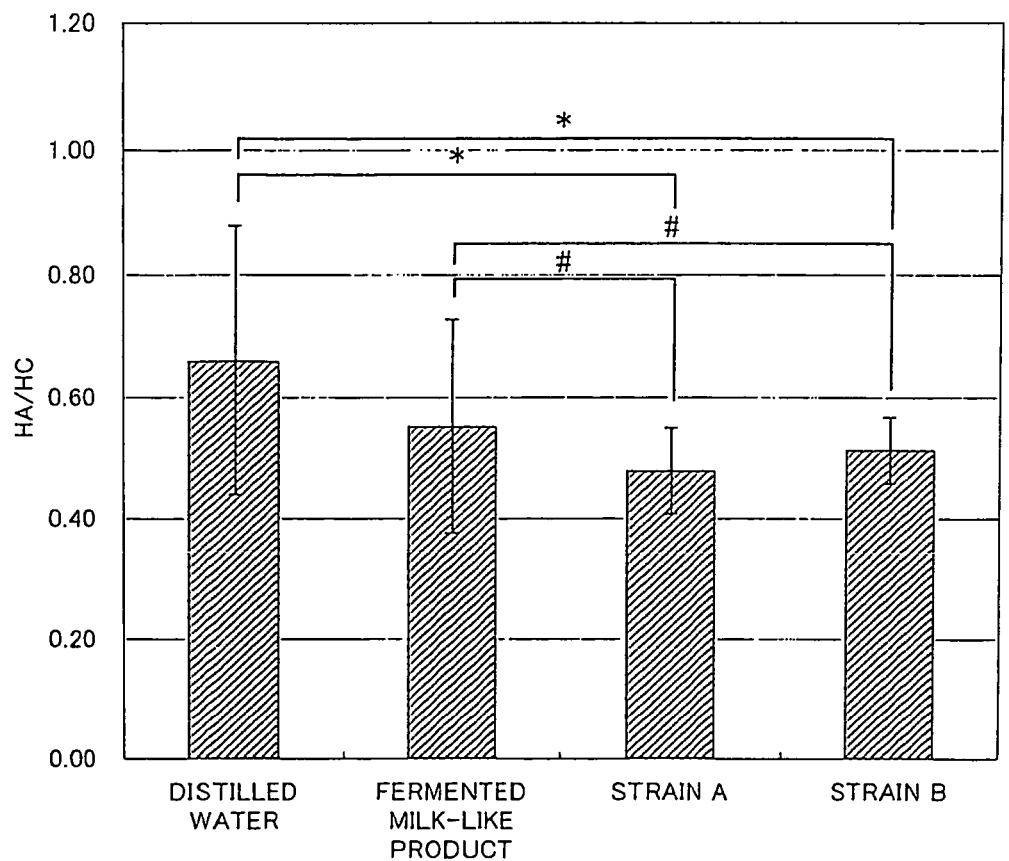
FIG. 3 shows a comparison of g=2.49 signals of liver tissue after administration of specimens for 60 days.

Evaluation of Signal Intensity:

The results of the EPR measurement after standardization of signal intensity as described above are shown in FIG. 3. When significant difference by statistic treatment was confirmed, a mark "#" ($P<0.10$) or "*" ($P<0.05$) is put according to the significance level. Efficacy was indicated by a lactic acid bacterium, *Lactobacillus* sp CP3012 (FERM BP-8052), and *Bacillus subtilis* c-3102 (FERM BP-1096) over the control treatment.

Measurement of Concentration of cPCB in Liver Tissue:

After 2 g of liver tissue was put into a mortar and homogenized with anhydrous sodium sulfate (for PCB analysis use, manufactured by Kanto Kagaku Corporation), the resulting mixture was put into circular cylinder filter paper to carry out Soxhlet extract for 7 hours using 200 ml of a mixed solution of diethyl ether and hexane (both for residual agricultural chemical test use, manufactured by Kanto Kagaku Corporation) at a rate of 3:1. The extract solution was concentrated in a KD condenser to the volume of 10 ml or less. To the concentrate, added were 50 ml of 1N potassium hydroxide (special grade, manufactured by Wako Pure Chemical Ind., Ltd.) using ethanol (for residual agricultural chemical test use, manufactured by Kanto Kagaku Corporation) as a solvent and 100 μl of a $C^{13}$ mass labeled standard mixed solution (manufactured by Wellington Laboratories; 3,3',4,4'-T4CB, 3,3',4,4',5-P5CB,3,3',4,4',5,5'-H6CB was diluted to special grade nonane and adjusted to 60 pg/μl), followed by saponification under reflux at 100° C. for 1 hour. The content solution was moved to a separatory funnel, and 50 ml of hexane (the same as described above) and 50 ml of distilled water washed by hexane were added thereto, followed by extraction under shaking for 15 minutes. An organic solvent layer was collected, was dehydrated with anhydrous sodium sulfate (the same as described above), and was concentrated to the volume of 5 ml using a KD condenser under airflow of high purity (99.99%) nitrogen. The concentrate was developed in an activated silica gel column. Silica gel (Wako-gel S-1; manufactured by Wako Pure Chemical Ind., Ltd.) was heated at 130° C. for 3 hours, and 1.5 g thereof was suspended to n-hexane (the same as described above) and was wet-packed in a glass column having an internal diameter of 10 mm to thereby the activated silica gel column. Development was carried out at a flow rate of 1 drop per second using n-hexane. A total volume of 150 ml was fractionated, the total volume was shaken with 10 ml of concentrated sulfuric acid (of a special grade; manufactured by Wako Pure Chemical Ind., Ltd.) at a separatory funnel, and the operation was repeated until staining of sulfuric acid was disappeared. Next, washing was carried out with distilled water which had been washed with hexane until an aqueous layer became neutral, dehydration was carried out with anhydrous sodium sulfate (the same as described above), concentration was carried again to the volume of 100 µl or less using the KD condenser, and toluene (for dioxin analysis use, manufactured by Kanto Kagaku Corporation) was added thereto to give the volume of 100 µl. The thus obtained sample was analyzed by a gas chromatograph mass spectrometer (GC-MS). For GC-MS, MStation (manufactured by JEOL) attached with SPB-Octyle (50 cm×0.2 mm×0.25 µm; manufactured by SUPELCO) was used, and measurement was carried out by the HR-SIM method with the resolution 8,000 or more.

Figure 4:
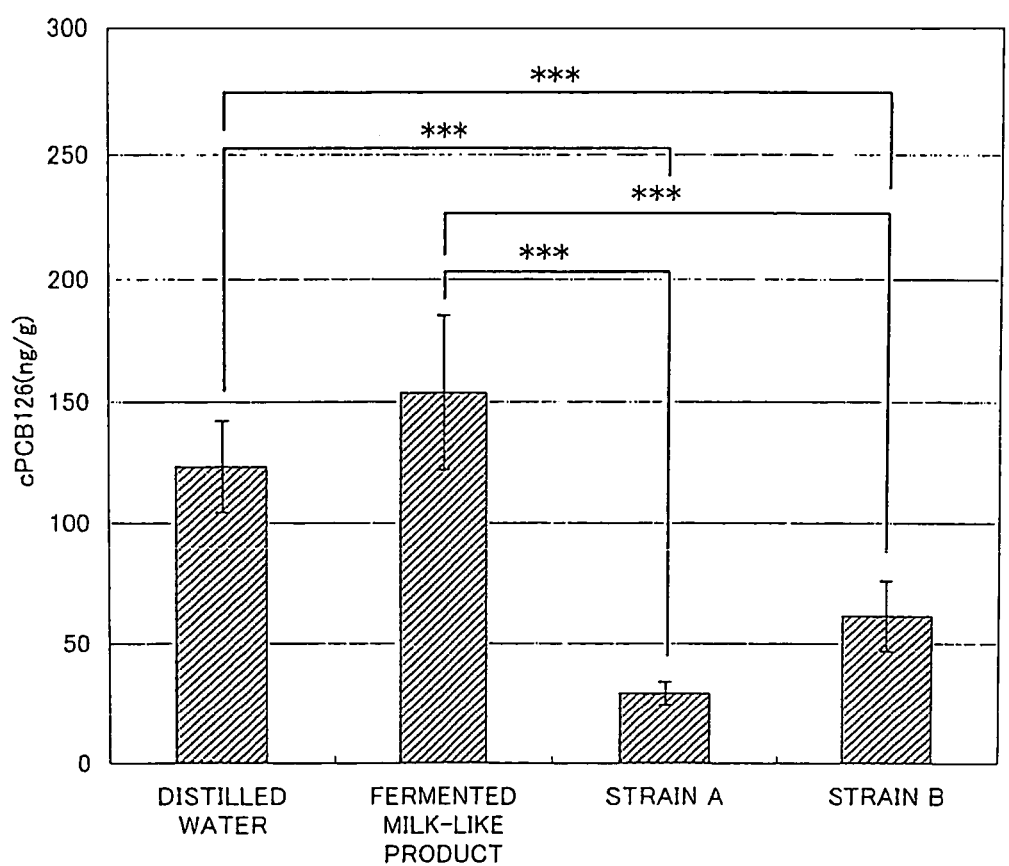
FIG. 4 shows a comparison of concentration of PCB126 in liver tissue after administration of specimens for 60 days.

Evaluation of Concentration of cPCB Inside Liver:

FIG. 4 shows comparison of concentrations of cPCB126 obtained by the results of the GC-MS measurement for the liver tissue. When significant difference by statistic treatment was confirmed, a mark "***" ($P<0.001$) is put according to the significance level. In the same manner as the result of the ESR measurement, efficacy was indicated by a lactic acid bacterium, *Lactobacillus* sp CP3012 (FERM BP-8052), and *Bacillus subtilis* c-3102 (FERM BP-1096) over the control treatment.

This application is based on Japanese application No. 2002-160055 filed on May 31, 2002, the entire contents of which are incorporated hereinto by reference.

While the invention has been described in detail and with reference to specific embodiments thereof, it will be apparent to one skill in the art that various changes and modifications can be made therein without departing from the spirit and scope thereof. All references cited herein are incorporated in their entirety.

INDUSTRIAL APPLICABILITY

The accelerating agent of the present invention can be used in foods, drinks and the like because it restores the effect of cytochrome P450 protein previously denatured and deactivated by dioxins and promotes spontaneous action of excretion thereof. In addition, safe meat in which accumulation of dioxins is little can be supplied by utilizing the accelerating agent to feeds for feedstock.

The invention claimed is:

1. A method for treating a subject having an amount of dioxin in the liver characterized by the appearance of a peak at g=2.49 as measured in a liver sample by EPR comprising:
   administering to said subject *Bacillus subtilis* c-3102 (accession number FERM BP-1096) in amount of $10^6$ cells/kg of body weight or more per day.

2. The method of claim 1, wherein said subject is human.
3. The method of claim 1, wherein said subject is a livestock animal that is edible.
4. The method of claim 1, wherein said subject is a cow.
5. The method of claim 1, wherein said subject is a pig.
6. The method of claim 1, wherein said subject is a chicken.
7. The method of claim 1, wherein said subject is a farmed fish.
8. The method of claim 1, wherein said administration is oral administration.
9. The method of claim 1, wherein said administration is oral administration of a food or feed containing the *Bacillus subtilis* c-3102.
10. The method of claim 1, wherein said subject is a livestock animal that is edible and wherein said administration is oral administration.
11. The method of claim 1, wherein said dioxin is at least one selected from the group consisting of polychlorodibenzo-p-dioxins (PCDDs), polychlorinated dibenzofurans (PCDFs), co-planar polychlorinated biphenyls (cPCBs), and isomers thereof.
12. The method of claim 1, wherein said subject is suffering from dioxin toxicity.
13. The method of claim 1, wherein said subject has dioxin-related hepatopathy.
14. The method of claim 1, wherein the height of the peak at g=2.49 is reduced in the subject after administration of *Bacillus subtilis* c-3102 compared to the height of the peak prior to administration of the *Bacillus subtilis* c-3102.
15. A method for treating a human subject having an amount of dioxin in the liver characterized by the appearance of a peak at g=2.49 as measured in a liver sample by EPR comprising:
   administering to said subject *Bacillus subtilis* c-3102 (accession number FERM BP-1096) in an amount sufficient to reduce the amount of denatured P-450 indicated by the peak at g=2.49.
16. The method of claim 15, which comprises administering *Bacillus subtilis* c-3102 in an amount of $10^6$ cells/kg of body weight or more per day.
17. The method of claim 15, which comprises administering *Bacillus subtilis* c-3102 in an amount of $5 \times 10^9$ cells/kg of body weight or more per day.
18. The method of claim 1, which comprises administering *Bacillus subtilis* c-3102 in an amount of $5 \times 10^9$ cells/kg of body weight or more per day.
19. The method of claim 1, wherein said administration is oral administration and said *Bacillus subtilis* c-3102 is administered in a food comprising fermented milk, yogurt, a lactic acid drink, an acidophilus milk or other dairy product.
20. The method of claim 1, wherein said administration is oral administration and said *Bacillus subtilis* c-3102 is administered in a food comprising natto, fermented soybeans, rice malt or other solid fermented food.
21. The method of claim 1, wherein said administration is oral administration and said *Bacillus subtilis* c-3102 is administered in the form of a powder or tablet.
22. The method of claim 1, wherein said administration is oral administration and said *Bacillus subtilis* c-3102 is administered in combination with a carrier or excipient.
23. The method of claim 1, further comprising administering at least one other lactic acid bacteria, nonpathogenic *Bacillus* or bifidobacteria.

* * * * *